(12) United States Patent
Tu et al.

(10) Patent No.: US 6,319,251 B1
(45) Date of Patent: Nov. 20, 2001

(54) MEDICAL DEVICE AND METHODS FOR TREATING INTRAVASCULAR RESTENOSIS

(76) Inventors: Hosheng Tu; Steve Chun-Guang Tu, both of 2151 Palermo, Tustin, CA (US) 92782

(*) Notice: Subject to any disclaimer, the term of this patent is extended or adjusted under 35 U.S.C. 154(b) by 0 days.

(21) Appl. No.: 09/489,688

(22) Filed: Jan. 24, 2000

Related U.S. Application Data

(63) Continuation-in-part of application No. 09/159,697, filed on Sep. 24, 1998, now Pat. No. 6,036,689.
(51) Int. Cl.$^7$ .................................................. A61B 18/18
(52) U.S. Cl. ........................ 606/41; 607/102; 607/122; 606/194; 606/198
(58) Field of Search ...................... 606/41–50, 190–192, 606/194, 198; 607/122, 101, 102, 113

(56) References Cited

U.S. PATENT DOCUMENTS

| | | | |
|---|---|---|---|
| 5,078,736 | * 1/1992 | Behl et al. ........................ | 606/41 |
| 5,575,810 | * 11/1996 | Swanson et al. ................... | 606/41 |
| 5,722,403 | 3/1998 | McGee et al. ..................... | 128/642 |
| 5,735,869 | * 4/1998 | Fernandez-Aceytuno ........... | 606/194 |
| 5,941,869 | * 8/1999 | Patterson et al. .................. | 606/41 |
| 6,179,824 | * 1/2001 | Essers et al. ...................... | 604/28 |

* cited by examiner

*Primary Examiner*—Linda C. M. Dvorak
*Assistant Examiner*—David M. Ruddy

(57) ABSTRACT

A medical device for treating intravascular restenosis of a patient, the medical device comprising a catheter shaft and an inner catheter, the inner catheter having a deployable wire assembly arrangement, wherein the deployable wire assembly arrangement comprises a plurality of preshaped expandable metallic basket members at the distal end of the inner catheter adapted to contact a pre-implanted stent and to apply RF current to the tissues for therapeutic purposes through a wire guide shaft. Alternately, a plurality of expandable metallic basket members are secured to the distal section of the catheter shaft for contacting a pre-implanted stent of the patient through a wire guide shaft.

16 Claims, 8 Drawing Sheets

MEDICAL DEVICE AND METHODS FOR TREATING INTRAVASCULAR RESTENOSIS

CROSS-REFERENCE TO RELATED APPLICATIONS

This patent application is a continuation-in-part application of application Ser. No. 09/159,697, entitled "Ablation Device for Treating Atherosclerotic Tissues" filed Sep. 24, 1998, U.S. Pat. No. 6,036,689 now allowed by the U.S. Patent Office, and is incorporated herein by reference.

TECHNICAL FIELD OF THE INVENTION

The present invention generally relates to improved medical device and methods for treating tissues, and more particularly, to such an ablation device and methods for treating atherosclerotic tissues in a patient by delivering therapeutic RF energy through an expandable basket structure having means for providing a plurality of continuous linear metallic wires assemble to the specific lesion sites.

BACKGROUND OF THE INVENTION

An artery is one of the tube-shaped blood vessels that carry blood away from a heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Recently, a new technique of inserting a metallic stenting element is used to permanently maintain the walls of the vessel treated at its extended opening state. Vascular stents are tiny mesh tubes or coils made of stainless steel or other metals and are used by heart surgeons to prop open the weak inner walls of diseased arteries. A catheter with a flexible guidewire-type tip is threaded up from the arm or groin through the artery until it reaches the blocked area. The stent is then deployed via an inflated balloon or via a delivery catheter. The deployed stent ruptures the plaque and increases the diameter of the blood vessel opening. The arterial passage is thus widened. As a result of enlarging the hardened plaque, cracks may unfortunately occur within the plaque to expose the underlying fresh tissue or denuded cells to the blood stream.

There are limitations, however, to this technique's application, depending on the extent of the disease, the blood flow through the artery, the part of the anatomy, and the particular vessels involved. Plaque build-up and/or severe re-stenosis recurrence within 6 months is generally up to 20-30 percent of those treated. The underlying newly exposed fresh collagen tissue or damaged cells still pose as a precursor for vessel reclosures or restenosis, regardless of stenting or not.

When a clogged artery is widened, the plaque or atheromatous material is broken up or split open while stretching the remaining soft parts of the vascular and perivascular tissue. Thus, stenting achieves its goal by creating a controlled but substantial injury to the vessel wall. However, the underlying collagen, tissue or damaged endothelium is exposed to the blood flow. Collagen has a pro-thrombotic property, which is part of the body healing processes. Furthermore, collagen has been widely used in hemostat treatment owing to its clotting properties. Unless the newly exposed collagen or the damaged endothelium is passivated or modulated, the chance for blood vessel clotting as well as restenosis still exists. Moderate heat is known to tighten and shrink the collagen tissue as illustrated in U.S. Pat. Nos. 5,456,662 and 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36-44, August 1998). Therefore, it becomes imperative to post-treat vessel walls after the walls have been treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissue contact site to obtain the desired temperature for treating a tissue.

To effect the optimal ablation, it requires selection of the most appropriate device-to-tissue contact site as well as the most effective contact surface area. Several recent patents disclose a catheter in a basket structure having means for providing a plurality of discrete and isolated point electrodes. The patents include U.S. Pat. No. 4,699,147 to Chilson et al., U.S. Pat. No. 5,156,151 to Imran, U.S. Pat. No. 5,255,679 to Imran, U.S. Pat. No. 5,345,936 to Pomeranz et al., U.S. Pat. No. 5,411,025 to Webster, Jr., U.S. Pat. No. 5,628,313 to Webster, Jr., U.S. Pat. No. 5,636,634 to Kordis et al., and U.S. Pat. No. 5,672,153 to Lax et al. However, all of the above-identified patents comprise a non-conductive spacing between any two electrodes. A major drawback of those patents is obvious because of its limited electrode contact surface to the tissues for delivering heat therapy.

McGee et al. in U.S. Pat. No. 5,722,403 discloses a combination of a balloon and electrode arrangement for treating tissue. However, McGee et al. does not disclose a medical device comprising a plurality of continuous wire electrodes for contacting an implanted stent to treat the underlying exposed tissue for minimizing intravascular restenosis.

A stent deployed within a vessel, such as a coronary stent, has excellent metal-to-tissue contact surface. It becomes an ideal medium for applying thermal energy to the specific tissue that has been enlarged and has newly tissue exposed. The metal-to-tissue contact site is the tissue region that most urgently needs heat treatment or modulation. A RF delivery means for contacting the metallic stenting element is useful in this case to shrink and tighten the target tissue for treating intravascular restenosis. Particularly, a wire assembly arrangement comprising a plurality of deployable metallic members, such as the long continuous wires on a basket-type catheter shaft, is useful for delivering the RF thermal energy to the denuded collagen or damaged endothelium via a pre-implanted stent to shrink and tighten the target tissue after a stent-assisted angioplasty procedure.

Therefore, there is a need for an improved medical device having the capability to effectively contact the inner walls of a tubular vessel via a pre-implanted stent using the radiofrequency energy to treat an enlarged artery or other tissues, such as esophagus, larynx, ureter, urethra and the like.

SUMMARY OF THE INVENTION

In general, it is an object of the present invention to provide a method and an improved medical ablation device for generating heat, to treat the atherosclerotic vascular vessels, or other tissues/organs, such as intestine, colon, uterus, urethra tube, and the like. It is another object of the present invention to provide a method and a device for monitoring the temperature of the ablated tissue, and to control the temperature by utilizing a temperature control mechanism and/or algorithm. The location of the temperature sensor means is preferably at close proximity of the metal-to-tissue contact sites of the ablation device. It is still another object of this invention to provide a method and an device for treating atherosclerotic tissues, vascular walls, or tubular cellular tissues by applying RF current to the metallic members of a basket-type catheter system having a plurality of metallic wires assembly arrangement and subsequently to the underlying tissues. It is a further object of the present invention to apply RF current via a basket-like wire assembly arrangement through a pre-implanted stent to the underlying tissue for therapeutical purposes.

Briefly, heat is generated by supplying a suitable RF energy source to a device having a RF current delivery arrangement, combining with a pre-implanted stent as an electrode arrangement for contacting the body tissues. "An electrode arrangement" is defined in this invention as a combination of a metallic structure that is accessible to a RF current source and a pre-implanted stent, wherein the pre-implanted stent in a patient is not part of the medical device of the present invention. The medical device system comprising a metallic structure is generally referred to as a flexible catheter having a plurality of basket members, wherein each basket member is a linear continuous metallic wire arrangement. Each basket member may be in a mesh form, a coil form, a curved wire form, or other appropriate form, used to contact the pre-implanted stent. The basket member of this invention that has a continuous conductive wire arrangement is different from a conventional electrophysiology catheter which usually has a plurality of electrodes, the electrodes being separated by a non-conducting zone.

The energy can be applied to the metallic basket member and subsequently to the atherosclerotic vascular walls or cellular tissues through the pre-implanted stent in a patient. A DIP (dispersive indifferent pad) type pad or electrode that contacts the patient, is connected to the Indifferent Electrode Connector on the RF generator. Therefore, the RF current delivery becomes effective when a close circuit from a RF generator through a patient and returning to the RF generator is formed. Heat is controlled by the power of the RF current delivered, by the delivery duration, and by the delivery mode. The standard RF current generator and its applications through the electrode arrangement to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion of the catheter shaft is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the medical device comprises a deployable wire assembly arrangement, wherein the wire assembly arrangement and a pre-implanted stent of a patient forms an electrode arrangement for delivering RF current to a tissue for treating intravascular restenosis. In a preferred embodiment, the medical device system for treating intravascular restenosis comprises a flexible catheter shaft having a distal section, a shaft distal end, a shaft proximal end, and at least one lumen extending between the shaft proximal end and the shaft distal end, wherein the at least one lumen has at least one opening at the shaft distal end. A handle is attached to the shaft proximal end, wherein the handle has a cavity. In one embodiment, the medical device system may further comprise an inner catheter located inside the at least one lumen of the catheter shaft, wherein the inner catheter comprises a distal end and a proximal end.

The wire assembly arrangement may be mounted at the distal end of the inner catheter, wherein the wire assembly arrangement comprises a plurality of preshaped expandable metallic basket members, each metallic basket member having a member distal end, a member proximal end, wherein the member proximal ends of the preshaped expandable metallic basket members are joined at the distal end of the inner catheter and wherein the member distal ends of the preshaped expandable metallic basket members are joined at a distal joint. Furthermore, a wire assembly deployment mechanism for deploying the wire assembly arrangement is mounted on the handle, wherein the wire assembly deployment mechanism is coupled to the proximal end of the inner catheter, wherein the plurality of preshaped expandable metallic basket members are expanded at a deployed state, and wherein the plurality of preshaped expandable metallic basket members are retracted at a non-deployed state. The electrode arrangement is connected to an external RF generating means through an electrical conductor.

The medical device system may further comprise a wire guide shaft at the distal section of the catheter shaft, the wire guide shaft having a proximal end and a distal end, wherein the wire guide shaft defines a wire guide lumen, wherein the wire guide lumen has at least one opening at the distal end and at least one opening at the proximal end of the wire guide shaft, wherein the wire guide shaft is used for introducing said medical device system into a vascular vessel over a guidewire.

A method for treating intravascular restenosis of a patient having a pre-implanted stent, the method comprises delivering RF current to the pre-implanted stent so as to provide thermal therapy to the intravascular tissue for treating intravascular restenosis.

In another preferred embodiment, a medical device system for delivering RF current to a pre-implanted stent comprises a flexible catheter shaft having a distal section, a shaft distal end, a shaft proximal end, and at least one lumen extending between the shaft proximal end and the shaft distal end, wherein the at least one lumen has at least one opening at the shaft distal end of the catheter shaft. A handle is attached to the shaft proximal end of the catheter shaft, wherein the handle has a cavity. A wire assembly arrangement is mounted at the distal section of the catheter shaft, wherein the wire assembly arrangement comprises a plurality of preshaped expandable metallic basket members, each metallic basket member having a member distal end, a member proximal end, wherein the member proximal ends of the preshaped expandable metallic basket members are joined at the distal end of the catheter shaft and wherein the member distal ends of the preshaped expandable metallic basket members are joined at a basket distal joint. Furthermore, a wire assembly deployment mechanism for deploying the wire assembly arrangement is mounted on the handle, wherein the wire assembly deployment mechanism comprises an elongated element inside the at least one lumen of the catheter shaft, wherein a distal end of the elongated element is secured to the basket distal joint, wherein the plurality of preshaped expandable metallic basket members is expanded at a deployed state, and wherein the plurality of preshaped expandable metallic basket members is retracted at a non-deployed state.

The medical device comprises an external RF current generator, wherein the RF current is supplied to the wire assembly arrangement through an electric conductor for contacting a pre-implanted stent, wherein the wire assembly arrangement and the pre-implanted stent forms an electrode arrangement for delivering RF current to a tissue for therapeutic purposes.

The method and medical device of the present invention has several significant advantages over other known systems or techniques to treat the atherosclerotic tissues after the tissue is enlarged by an implanted stent. In particular, the device system comprising a deployable wire assembly arrangement having a plurality of linear continuous metallic wire arrangement for contacting a pre-implanted stent and using RF energy as a heat source in this invention results in a more efficient therapeutic effect, which is highly desirable in its intended applications.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of the medical device system, comprising applying radiofrequency energy therapy to treat the atherosclerotic vascular vessels, or other tubular cellular tissues of a patient through a basket-type medical device comprising a plurality of preshaped expandable metallic basket members and a pre-implanted stent of a patient.

Figure 1:
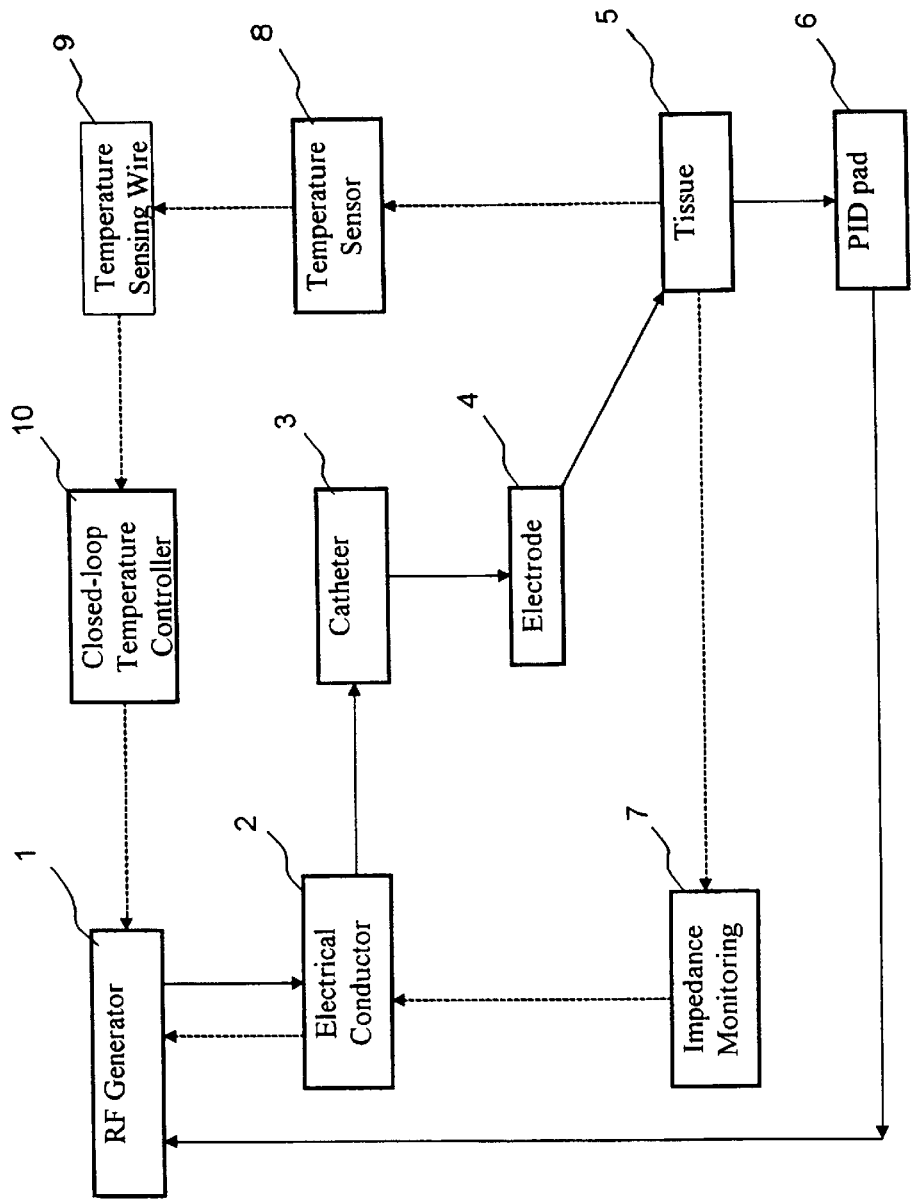
FIG. 1 is a schematic diagram of a RF treatment method in relation to the tissue or atherosclerotic tissue through an electrode arrangement in a patient.

FIG. 1 shows a schematic diagram of a RF treatment method in relation to the tissues or atherosclerotic tissues through an electrode arrangement in a patient. Since the patient already has a pre-implanted stent, the electrode arrangement is referred to hereby as a combination of a metallic structure of the medical device that is accessible to a RF current source and the pre-implanted stent. The metallic structure of the present invention may include a wire assembly arrangement comprising a plurality of metallic basket members for contacting the pre-implanted stent in a patient, wherein the metallic basket member has no non-conductive zone along a majority portion of the member. A RF generator 1 is connected to a catheter or a medical device 3 through an electrical conductor 2. An electrode arrangement 4 of the catheter 3 is to contact the tissue 5 of a patient when the device is deployed. The pre-implanted stent portion of the electrode arrangement 4 is in close contact with the underlying tissue 5. A DIP (dispersive indifferent pad) type pad 6 that contacts a patient is connected to the Indifferent Electrode Connector on the RF generator 1. Therefore, the RF current delivery becomes effective when a close circuit from a RF generator through a patient and returning to the RF generator is formed. Impedance 7 measured from the tissue contact may be used to ensure good tissue contact for tissue treatment, otherwise the RF current is cut off when the impedance is unreasonably high. A temperature sensor 8 may be used to measure the tissue temperature and is relayed through a temperature sensing wire 9 and a closed-loop temperature controller 10 for controlling the ablative energy delivered. Energy is controlled by the power of the RF current delivered, power delivery mode, and the delivery duration.

Figure 2:
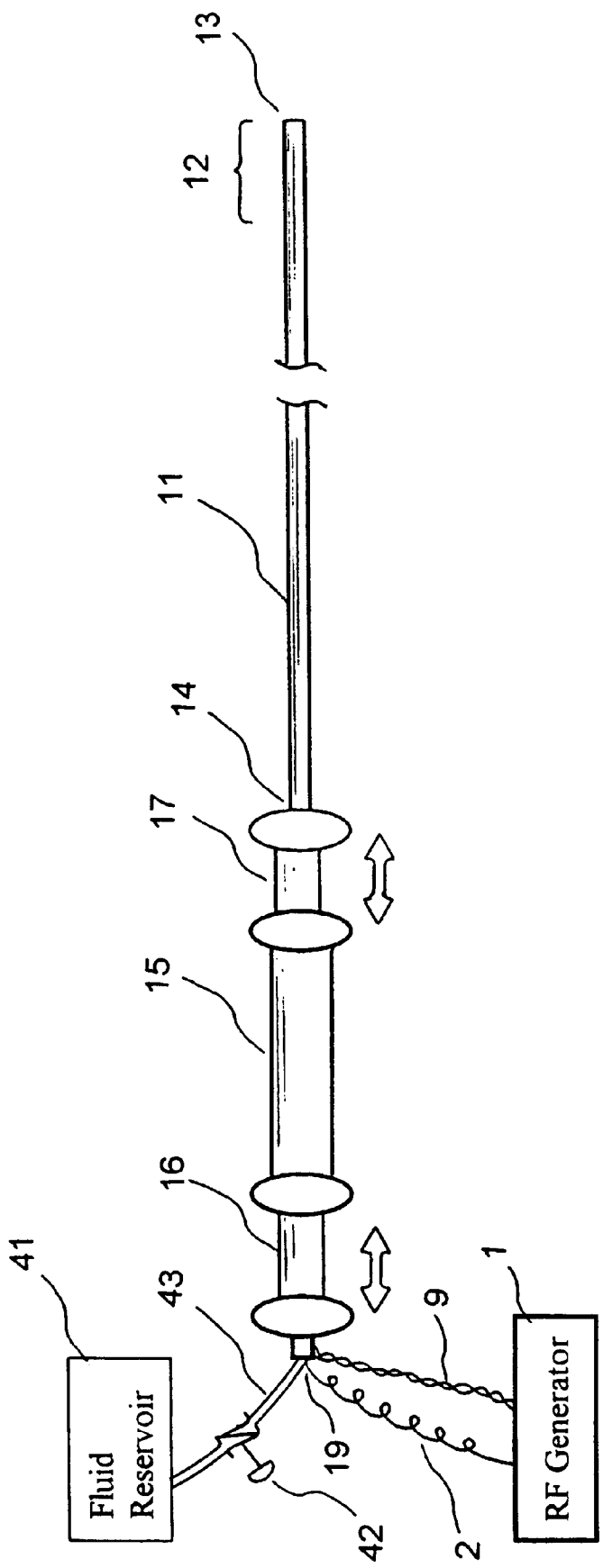
FIG. 2 is an overall view of the medical device system having a deployable wire assembly arrangement and a RF generator, constructed in accordance to the principles of the present invention.
Figure 3:
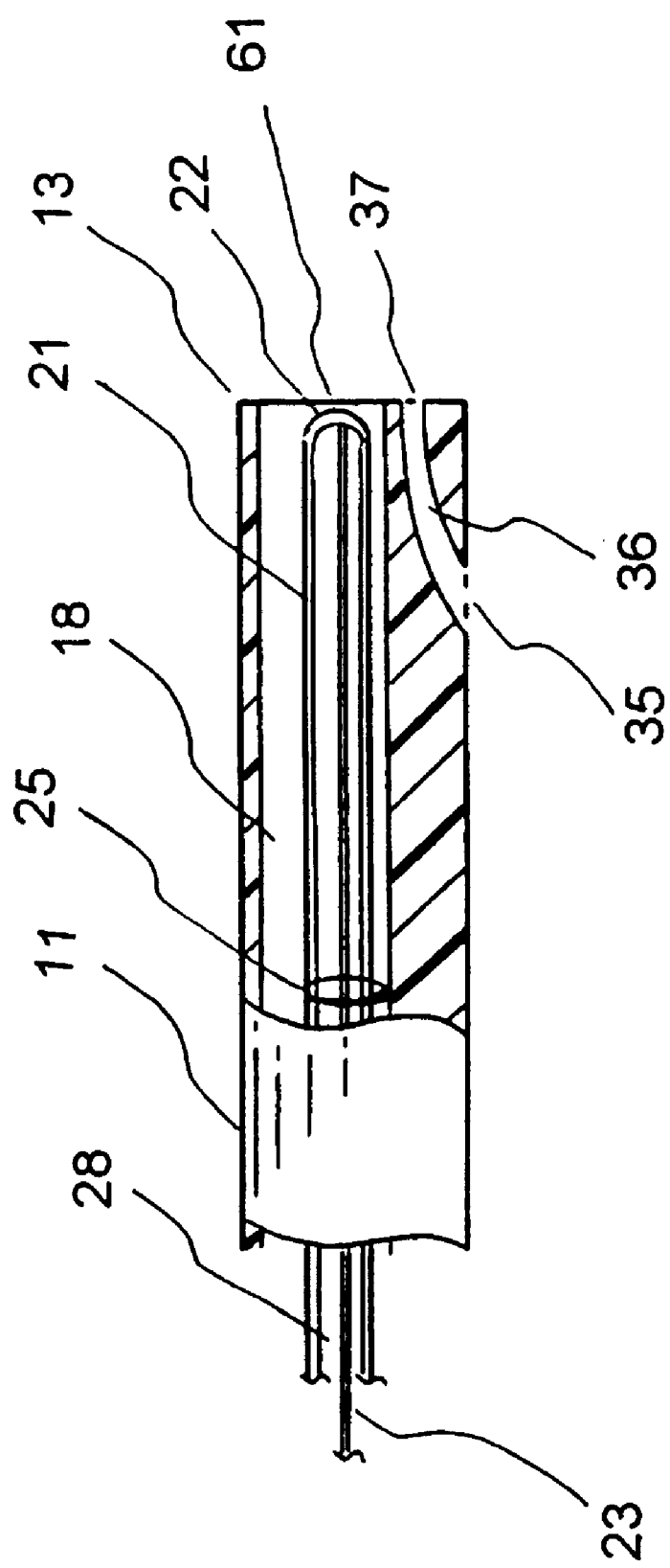
FIG. 3 is a cross-sectional view of the distal end portion of the device, the device having a deployable wire assembly arrangement positioned within the lumen of a flexible catheter shaft at a non-deployed state.

As shown in FIGS. 2 and 3, one preferred embodiment of the medical device system comprises a catheter shaft 11, the catheter shaft having a distal section 12, a shaft distal end 13, a shaft proximal end 14, and at least one lumen 18 extending between the shaft proximal end 14 and the shaft distal end 13, wherein the at least one lumen 18 may have at least one opening 61 at the shaft distal end 13 of the catheter shaft 11. A handle 15 is attached to the shaft proximal end 14 of the catheter shaft 11, wherein the handle 15 has a cavity.

In one preferred embodiment, an inner catheter 21 is located inside the at least one lumen 18 of the catheter shaft 11, wherein the inner catheter 21 comprises a distal end 25 and a proximal end. A wire assembly arrangement 44 is mounted at the distal end 25 of the inner catheter 21, wherein the wire assembly arrangement 44 may comprise either a plurality of non-preshaped expandable metallic basket members 4A–4B for wrapping around an inflatable balloon or a plurality of preshaped expandable metallic basket members 4I–4L and/or 4M–4Q, each metallic basket member having a member distal end, a member proximal end, wherein the member proximal ends of the expandable metallic basket members are joined at the distal end 25 of the inner catheter 21 and wherein the member distal ends of the expandable metallic basket members are joined at a distal joint 22.

A wire assembly deployment mechanism 17 may be mounted on the handle 15, wherein the wire assembly deployment mechanism 17 is attached to the proximal end of the inner catheter 21, wherein the plurality of preshaped expandable metallic basket members are expanded at a deployed state, and wherein the plurality of preshaped expandable metallic basket members are retracted at a non-deployed state. During the insertion into or removal of the medical device from a patient, the wire assembly arrangement is at a non-deployed state.

Figure 5:
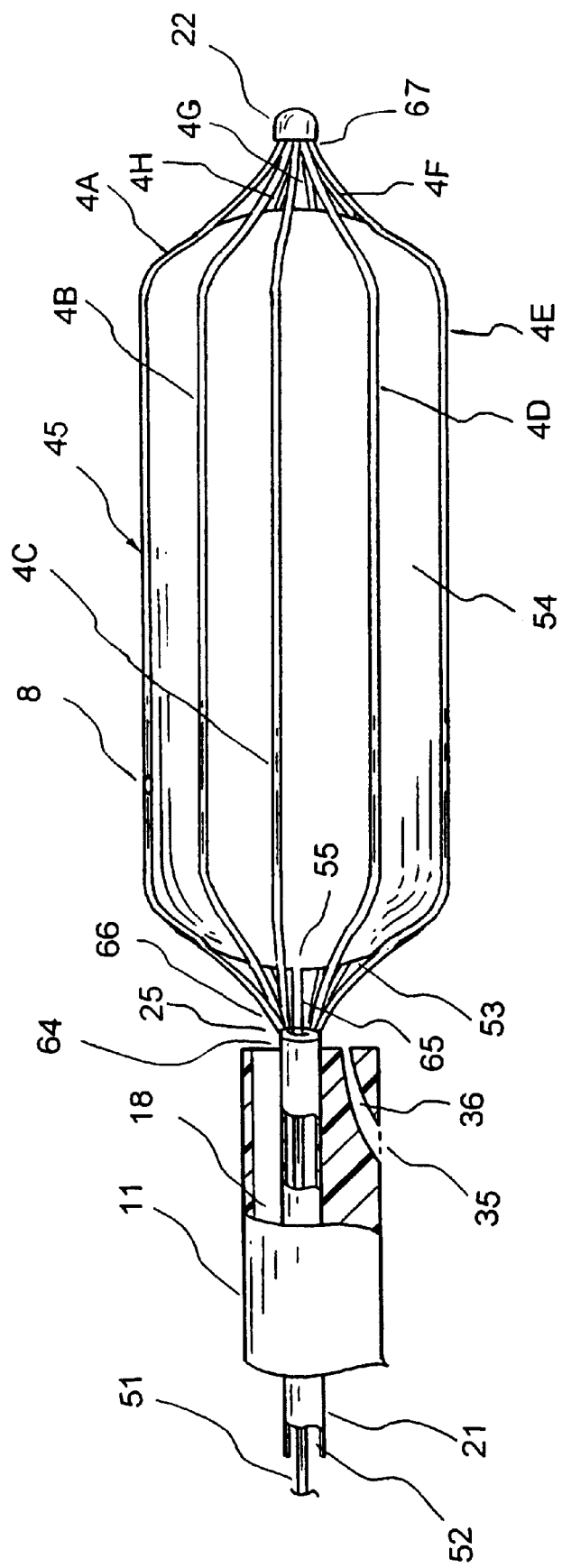
FIG. 5 is a cross-sectional view of the distal end portion of a preferred medical device, the device having a deployable wire assembly arrangement comprising a plurality of expandable metallic basket members wrapped onto and around an inflatable balloon at a deployed state.

The medical catheter system of the present invention further comprises a RF current generating means 1 for generating RF current, wherein the RF current is supplied to the wire assembly arrangement 44, 45, 46 for therapeutic purposes. The RF current is supplied through an electric conductor 2 for contacting a pre-implanted stent in a patient. The wire assembly arrangement 44, 45, 46 and the pre-implanted stent forms an electrode arrangement 4 for delivering RF current to a tissue for treating intravascular restenosis. In an alternate embodiment as shown in FIG. 5, a fluid reservoir 41 may be provided for delivering pressurized working fluid through a control valve 42 and a conveying duct 43 to the inflatable balloon 53.

FIG. 3 shows a cross-sectional view of the distal end portion 12 of the device, wherein the device has a deployable wire assembly arrangement 44 positioned within the lumen 18 of the inner catheter 21 at a non-deployed state. In one embodiment, the shaft distal end 13 has two lumens 18 and 36. One lumen 18 is used by the deployable inner catheter 21. The other lumen 36, a wire guide lumen is used to tract and ride on a previously inserted guidewire to the lesion site. In an alternate embodiment, the medical device of the present invention rides on an existing guidewire to the target site 5 for ablation operation.

An insulated electrical conductor 2 or the inner catheter itself 21 serving as a conducting means passes through the lumen 18 of the catheter shaft 11 and is connected to the wire assembly arrangement 44. The other end of the electrical conductor is connected to an external RF generator 1.

Figure 4:
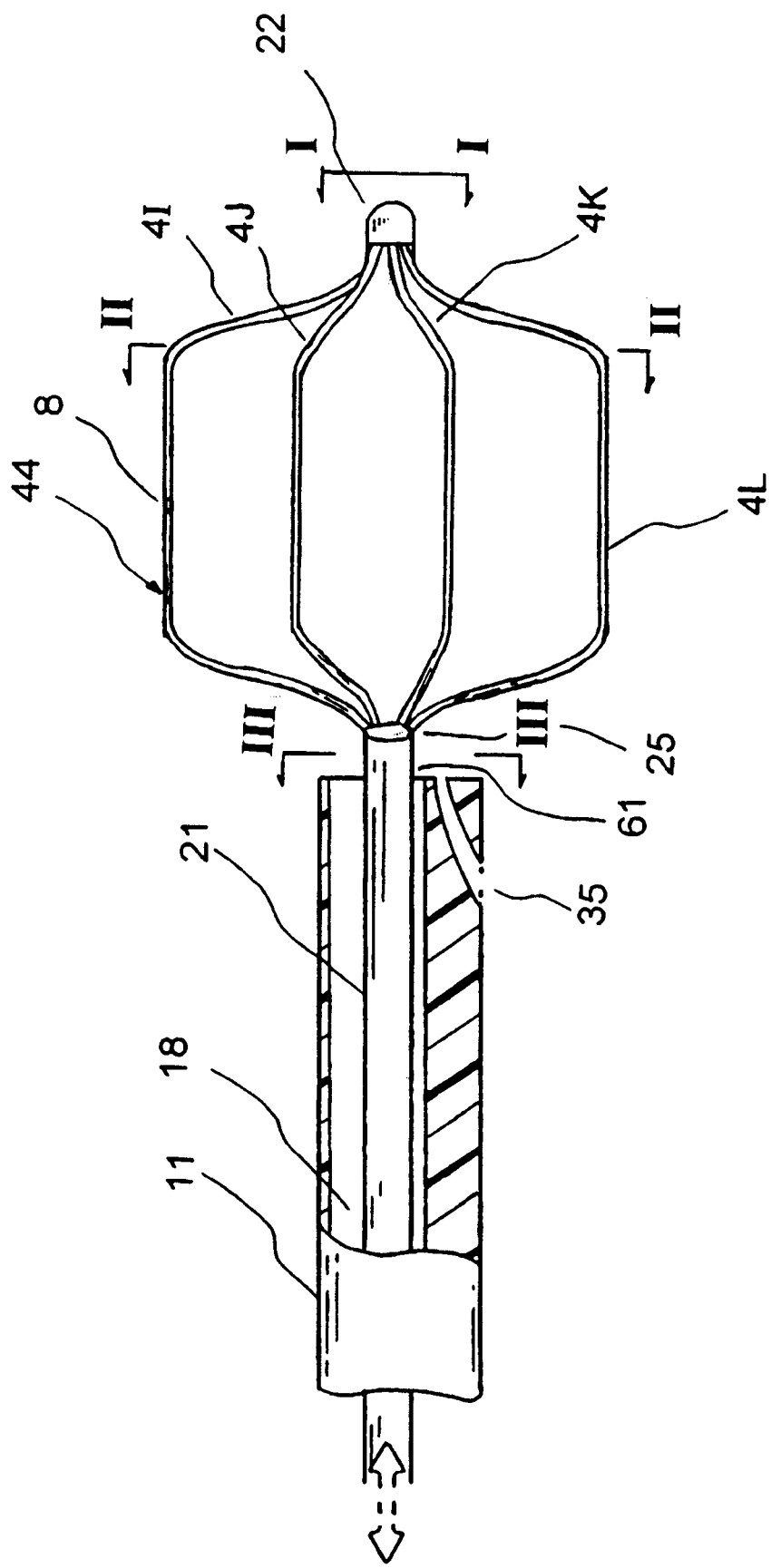
FIG. 4 is a cross-sectional view of the distal end portion of the device, the device having a deployable wire assembly arrangement comprising a plurality of preshaped expandable metallic basket members at a deployed state.

FIG. 4 shows a cross-sectional view of the distal end portion of the device, wherein the device has a deployable wire assembly arrangement 44 comprising a plurality of preshaped expandable metallic basket members at a deployed state. The deployment operation is initiated at the wire assembly deployment mechanism 17 at the handle 15. The deployed plurality of metallic basket members 4I, 4J, 4K, 4L are fully extended radially to contact an inside surface of the pre-implanted stent, as a result of its pre-shaped memory. This portion of the deployed metallic basket members is made of conductive material, which is externally connected to the RF current source through an insulated electrical conductor. Other portion of the catheter shaft and the surface of the inner catheter are generally not conductive.

In one embodiment, at least one temperature sensing means 8 may be disposed at close proximity of the wire assembly arrangement 44. Insulated temperature sensor wire means 9 passes from the temperature sensing means 8, to an external temperature control mechanism 10 through an outlet connector 19. The RF current delivery is controlled by using the measured temperature from the temperature sensing means 8, through a closed-loop temperature control mechanism 10 and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends about a signal to activate the RF current supply.

Figure 4A:
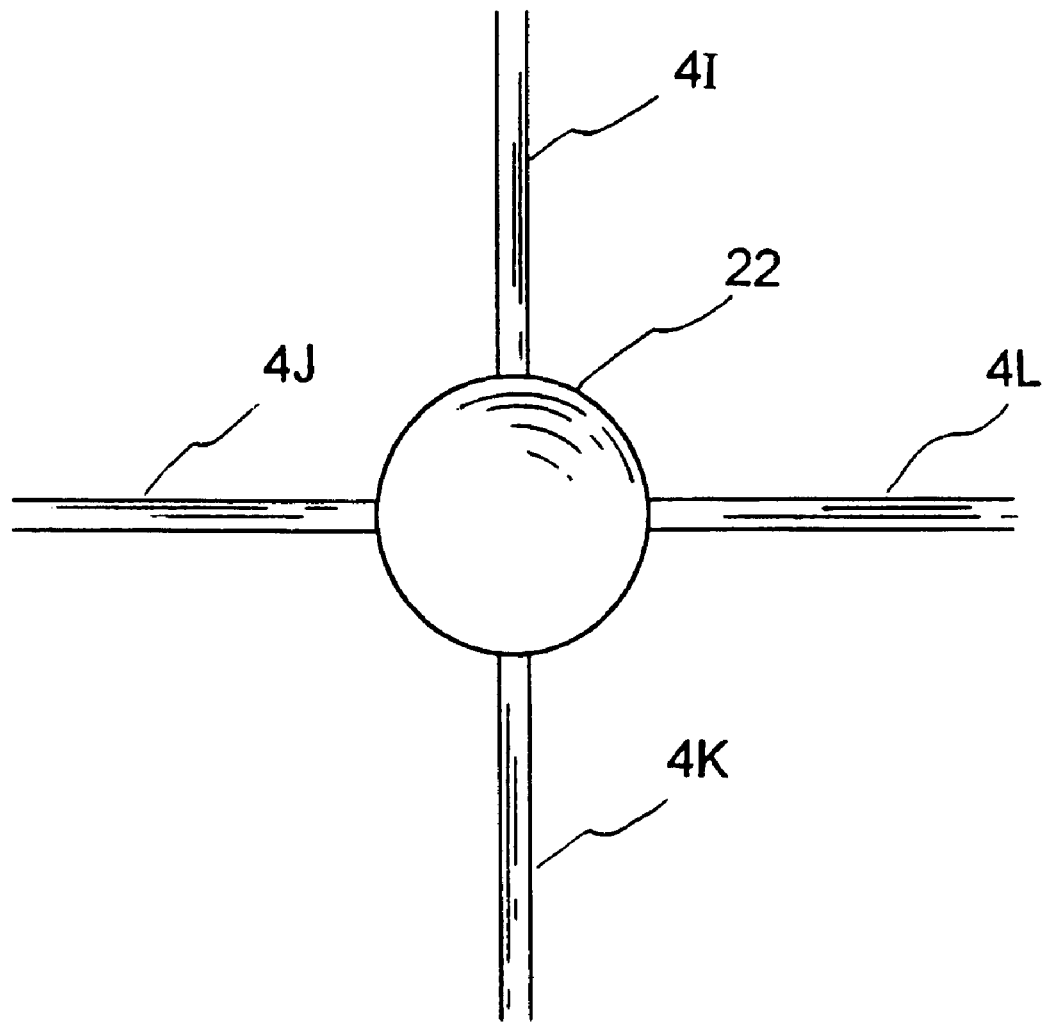
FIG. 4A is a transverse view, section I—I of FIG. 4.
Figure 4B:
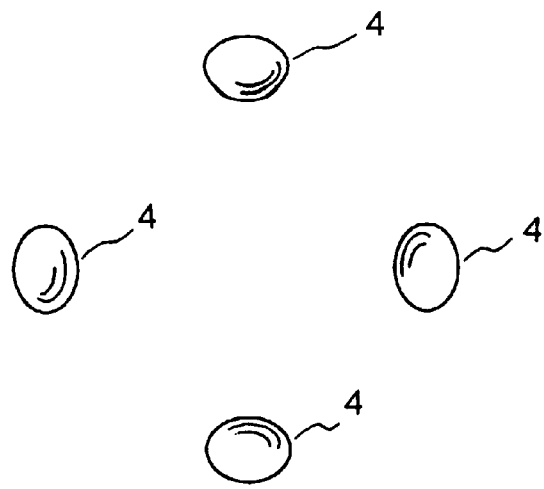
FIG. 4B is a transverse view, section II—II of FIG. 4.
Figure 4C:
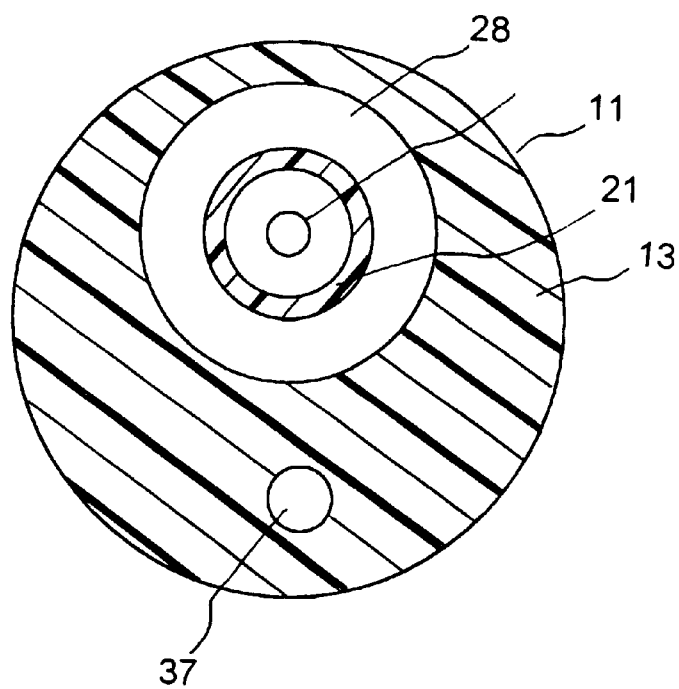
FIG. 4C is a transverse view, section III—III of FIG. 4.

FIG. 4A shows a transverse view, section I—I of FIG. 4. The distal ends of all metallic basket members 4I, 4J, 4K, and 4L are secured to a distal joint 22. FIG. 4B shows a transverse view, section II—II of FIG. 4. In one optional embodiment, the cross-section of the metallic basket members is an oval shape or flat shape. FIG. 4C shows a transverse view, section III—III of FIG. 4. In a preferred embodiment, a portion of the preshaped expandable metallic basket members is essentially straight at a deployed state.

FIG. 5 shows a cross-sectional view of the distal end portion of an alternate medical device, wherein the device has a deployable wire assembly arrangement 45 comprising a plurality of expandable metallic basket members wrapped onto and around an inflatable balloon at a deployed state. The alternate medical device system comprises a catheter shaft 11 having a distal section 12, a shaft distal end 13, a shaft proximal end 14, and at least one lumen 18 extending between the shaft proximal end 14 and the shaft distal end 13, wherein the at least one lumen 18 has at least one opening 64 at the shaft distal end 13 of the catheter shaft 11.

A handle 15 is attached to the shaft proximal end 14 of the catheter shaft 11, wherein the handle has a cavity. An inner catheter 21 is located inside the at least one lumen 18 of the catheter shaft 11, wherein the inner catheter 21 comprises a distal end 25, a proximal end, and at least one lumen 52 extending between the distal end and the proximal end. An inflation tubing 65 is an extension of an inflation lumen 51, wherein the inflation lumen 51 is located within the inner catheter 21 and is communicated to the external fluid reservoir 41 through the fluid conveying duct 43. The inflation tubing 65 extends distally to the distal end 25 of the inner catheter 21, the inflation tubing 65 having a proximal end and a distal end 55.

The alternate medical device further comprises an inflatable balloon 53 having a proximal end and a distal end, wherein the distal end 55 of the inflation tubing 65 opens into and is in communication with an interior of the inflatable balloon 53, the distal end of the inflatable balloon 53 is sealed. In the alternate medical device system, a wire assembly arrangement 45 is mounted at the digtal end 25 of the inner catheter 21, wherein the wire assembly arrangement comprises a plurality of expandable metallic basket members 4A–4H wrapped onto and around the inflatable balloon 53, each expandable metallic basket member having a member distal end 67 and a member proximal end 66, wherein the member proximal ends of the expandable metallic basket members are joined at the distal end 25 of the inner catheter 21 and wherein the basket distal ends of the expandable metallic basket members are joined at a distal joint 22. A wire assembly deployment mechanism 17 is mounted on the handle 15, wherein the wire assembly deployment mechanism 17 is attached to the proximal end of the inner catheter 21, wherein the plurality of expandable metallic basket members is expanded at a deployed state, and wherein the plurality of expandable metallic basket members is retracted at a non-deployed state.

Figure 6:
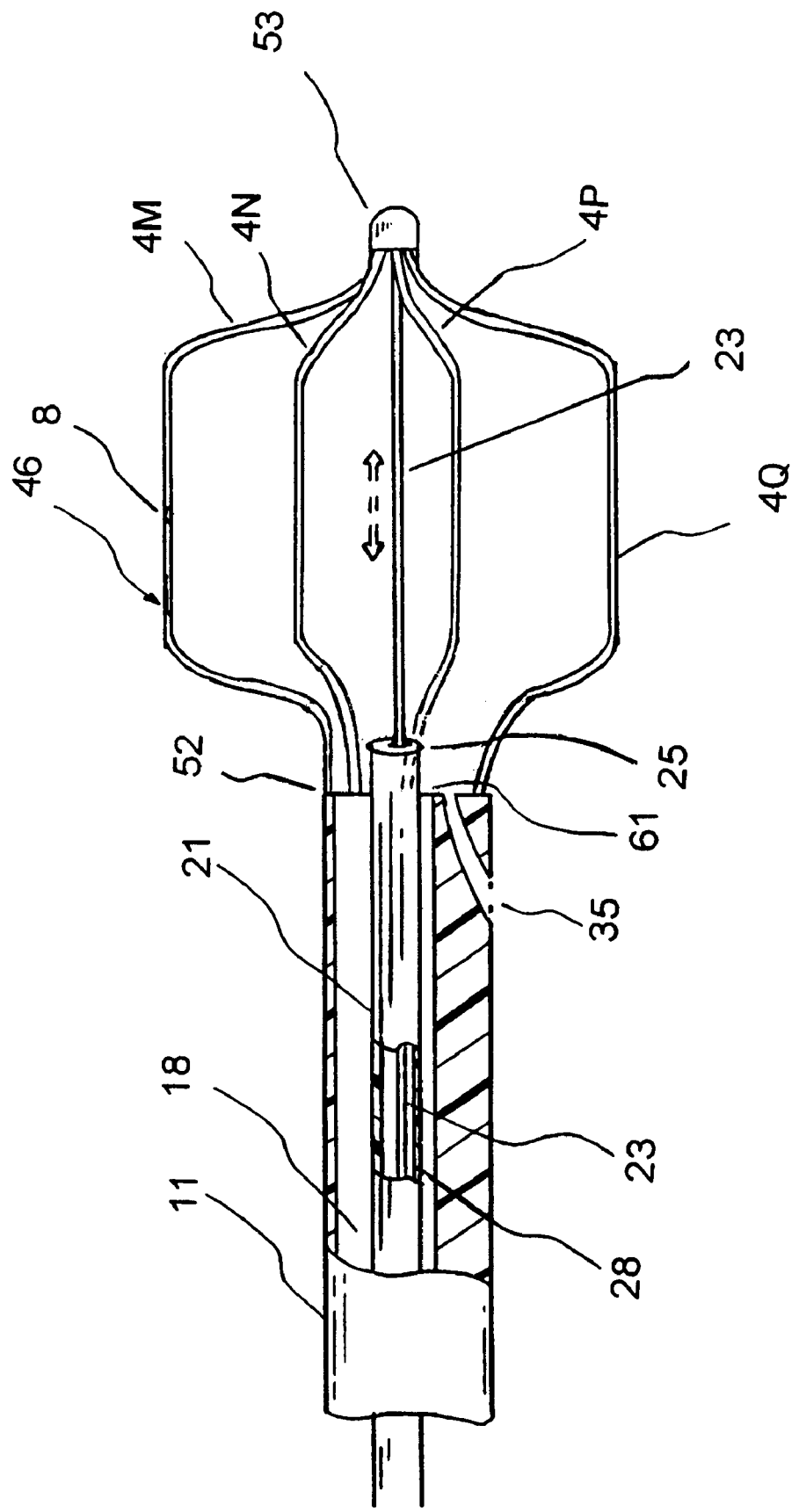
FIG. 6 is a cross-sectional view of the distal end portion of another preferred medical device, the device having a deployable wire assembly arrangement positioned at the distal section of a flexible catheter shaft at a deployed state.

As shown in FIG. 6, the medical device system may further comprise a lumen 28 between the proximal end and the distal end 25 of the inner catheter 21, and further comprises a connecting shaft 23 inside said lumen 28 of the inner catheter 21. The connecting shaft 23 has a distal end and a proximal end, wherein the distal end of the connecting shaft 23 is joined to the distal joint 53 of the metallic basket members, and wherein the proximal end of the connecting shaft is secured to the wire assembly deployment mechanism 17. A special push-pull controller 16 or the like on the handle adapted for the push-pull operation of the connecting shaft 23 is part of the wire assembly deployment mechanism 17. The wire assembly arrangement 46 is mounted at the distal section of the catheter shaft, wherein the wire assembly arrangement comprises a plurality of preshaped expandable metallic basket members 4M, 4N, 4P, 4Q, each metallic basket member having a member distal end, a member proximal end, wherein the member proximal ends of the preshaped expandable metallic basket members are joined at the distal end 52 of the catheter shaft 11 and wherein the member distal ends of the preshaped expandable metallic basket members are joined at a basket distal joint 53.

The medical device system also comprises a RF current generating means 1, wherein the RF current is supplied to the electrode arrangement 45 for therapeutic purposes.

The medical device system further comprises a wire guide shaft at the distal section 12 of the catheter shaft 11, the wire guide shaft defining a wire guide lumen 36, the wire guide shaft having a proximal end 35 and a distal end 37, wherein the wire guide lumen 36 hag at least one opening at the distal end and at least one opening at the proximal end of the wire guide shaft, wherein the wire guide shaft is used for introducing the medical device system into a vascular vessel over a guidewire. The wire guide lumen 36 may be located close to one side of the wire guide shaft for rapid exchange of the medical device system over the guidewire.

Alternatively, the medical device system may comprise a wire guide shaft at the distal section of the catheter shaft, the wire guide shaft defining a wire guide lumen, wherein the wire guide lumen is connected to and in communication with the at least one lumen 18 of the catheter shaft 11, the wire guide shaft having a proximal end and a distal end, wherein the wire guide shaft is used for introducing said medical device system into a vascular vessel over a guidewire.

A method for treating atherosclerotic tissues of a patient using a medical device system is illustrated. The medical device system may comprise a catheter shaft 11 and an inner catheter 21, the inner catheter having a proximal end, a distal end and a deployable wire assembly arrangement 44, 45, 46 mounted at the distal end of the inner catheter, wherein the wire assembly arrangement comprises a plurality of preshaped expandable metallic basket members, each metallic basket member having a member distal end, a member proximal end, wherein the member proximal ends of the metallic basket members are joined at the distal end of the inner catheter and wherein the member distal ends of the metallic basket members are joined at a distal joint. The device system further comprises a RF current generating means, wherein the RF current is supplied to the wire assembly arrangement. The method comprises the steps of: (a) inserting the medical device through an artery or a vein to the location of the atherosclerotic tissues; (b) deploying the wire assembly arrangement to expand the preshaped expandable metallic basket members adapted to contact a pre-implanted stent; and (c) applying RF current to the electrode arrangement to effect treatment of the atherosclerotic tissues.

As an alternative illustration, a method for treating atherosclerotic tissues of a patient using a medical device system of the present invention is illustrated. The method comprises the steps of: (a) inserting the medical device through an artery or a vein to the location of the atherosclerotic tissues; (b) deploying the wire assembly arrangement to expand the expandable metallic basket members adapted to contact a pre-implanted stent; and (c) applying RF current to the electrode arrangement to effect treatment of the atherosclerotic tissues. The alternate medical device system for delivering RF current to a pre-implanted stent may comprise a flexible catheter shaft having a distal section, a shaft distal end, a shaft proximal end, and at least one lumen extending between the shaft proximal end and the shaft distal end, wherein the at least one lumen has at least one opening at the shaft distal end of the catheter shaft.

A handle is attached to the shaft proximal end of the catheter shaft, wherein the handle has a cavity. A wire assembly arrangement is mounted at the distal section of the catheter shaft, wherein the wire assembly arrangement comprises a plurality of preshaped expandable metallic basket members, each metallic basket member having a member distal end, a member proximal end, wherein the member proximal ends of the preshaped expandable metallic basket members are joined at the distal end of the catheter shaft and wherein the member distal ends of the preshaped expandable metallic basket members are joined at a basket distal joint. A wire assembly deployment mechanism is mounted on the handle, wherein the wire assembly deployment mechanism comprises an elongated element inside the at least one lumen of the catheter shaft, wherein a distal end of the elongated element is secured to the basket distal joint, wherein the plurality of preshaped expandable metallic basket members is expanded at a deployed state, and wherein the plurality of preshaped expandable metallic basket members is retracted at a non-deployed state.

The external RF current generator means has the capability to supply RF current by controlling the time, power, and temperature through an optional separate closed-loop temperature control means. The patient is connected to the RF generator means through a DIP electrode to form a closed-loop current system. Therefore, RF current is supplied and delivered to the targeted atherosclerosis region, through the electrode arrangement of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode arrangement and by applying the vibrational pressure therapy, the atherosclerotic tissues can be treated.

In a particular embodiment, the material for the wire assembly arrangement of this invention consists of conductive metals such as platinum, iridium, gold, silver, stainless steel, Nitinol, or an alloy of these metals.

From the foregoing description, it should now be appreciated that a medical device system for the tubular organs, atherosclerotic tissues, and the treatment of vascular tissues, comprising a suitable energy source and a pre-implanted stent has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical device system for treating intravascular restenosis comprising:

a flexible catheter shaft having a distal section, a shaft distal end, a shaft proximal end, and at least one lumen extending between the shaft proximal end and the shaft distal end, wherein the at least one lumen has at least one opening at the shaft distal end;

a handle attached to the shaft proximal end, wherein the handle has a cavity;

an inner catheter located inside the at least one lumen of the catheter shaft, wherein the inner catheter comprises a distal end and a proximal end;

a wire assembly arrangement mounted at the distal end of the inner catheter, wherein the wire assembly arrangement comprises a plurality of preshaped expandable metallic basket members, wherein at least a portion of the preshaped expandable metallic basket members is essentially straight adapted for contacting a pre-implanted stent for treating intravascular restenosis, each metallic basket member having a member distal end, a member proximal end, wherein the member proximal ends of the preshaped expandable metallic basket members are joined at the distal end of the inner catheter and wherein the member distal ends of the preshaped expandable metallic basket members are joined at a distal joint;

a wire assembly deployment mechanism mounted on the handle, wherein the wire assembly deployment mechanism is coupled to the proximal end of the inner catheter, wherein the plurality of preshaped expandable metallic basket member are expanded at a deployed state, and wherein the plurality of preshaped expandable metallic basket members are retracted at a non-deployed state;

a wire guide shaft at the distal section of the catheter shaft, the wire guide shaft having a proximal end and a distal end that the wire guide shaft defines a wire guide lumen, wherein the wire guide lumen has at least one opening at the distal end and at least one opening at the proximal end of the wire guide shaft wherein the wire guide shaft is used for introducing said medical device system into a vascular vessel over a guidewire; and a RF current generating means for generating RF current, wherein the RF current is supplied to the wire assembly arrangement through an electric conductor for contacting a pre-implanted stent, wherein the wire assembly arrangement and the pre-implanted stent forms an electrode arrangement for delivering RF current to a tissue for treating intravascular restenosis.

2. The medical device system as in claim 1, wherein the wire guide lumen is at one side of the wire guide shaft for rapid exchange of said medical device system over the guidewire.

3. The medical device system as in claim 1, wherein the wire guide lumen is connected to and in communication with the at least one lumen of the catheter shaft, and wherein the wire guide shaft is used for introducing said medical device system over the guidewire.

4. The medical device system as in claim 1 further comprising at least one temperature sensor, wherein the temperature sensor is disposed at close proximity of the wire assembly arrangement of the inner catheter.

5. The medical device system as in claim 4 further comprising a temperature controller, wherein temperature measured from the temperature sensor is relayed to the temperature controller and is adapted to effect the RF current supply to the medical device system.

6. The medical device system of claim 1, wherein the RP current is within the range of 50 to 2,000 kHz.

7. The medical device system of claim 1, wherein material for the preshaped expandable metallic basket members of the wire assembly arrangement is selected from the group consisting of platinum, iridium, gold, silver, stainless steel, Nitinol, and an alloy of their mixtures.

8. A method for treating intravascular restenosis of a patient having a pre-implanted stent, the method comprising delivering RF current to the pre-implanted stent through a medical device system comprising:

a flexible catheter shaft having a distal section, a shaft distal end, a shaft proximal end, and at least one lumen extending between the shaft proximal end and the shaft distal end, wherein the at least one lumen has at least one opening at the shaft distal end;

a handle attached to the shaft proximal end, wherein the handle has a cavity;

an inner catheter located inside the at least one lumen of the catheter shaft, wherein the inner catheter comprises a distal end and a proximal end;

a wire assembly arrangement mounted at the distal end of the inner catheter, wherein the wire assembly arrangement comprises a plurality of preshaped expandable metallic basket members, each metallic basket member having a member distal end, a member proximal end, wherein the member proximal ends of the preshaped expandable metallic basket members are joined at the distal end of the inner catheter and wherein the member distal ends of the preshaped expandable metallic basket members are joined at a distal joint;

a wire assembly deployment mechanism mounted on the handle, wherein the wire assembly deployment mechanism is coupled to the proximal end of the inner catheter, wherein the plurality of preshaped expandable metallic basket members are expanded at a deployed state, and wherein the plurality of preshaped expandable metallic basket members are retracted at a non-deployed state;

a wire guide shaft at the distal section of the catheter shaft, the wire guide shaft having a proximal end and a distal end that the wire guide shaft defines a wire guide lumen, wherein the wire guide lumen has at least one opening at the distal end and at least one opening at the proximal end of the wire guide shaft, wherein the wire guide shaft is used for introducing said medical device system into a vascular vessel over a guidewire; and a RF current generating means for generating RF current, wherein the RF current is supplied to the wire assembly arrangement through an electric conductor for contacting the pre-implanted stent, wherein the wire assembly arrangement and the pre-implanted stent forms an electrode arrangement for delivering RF current to a tissue for treating intravascular restenosis.

9. A medical device system for delivering RF current to a pre-implanted stent comprising:

a flexible catheter shaft having a distal section, a shaft distal end, a shaft proximal end, and at least one lumen extending between the shaft proximal end and the shaft distal end, wherein the at least one lumen has at least one opening at the shaft distal end of the catheter shaft;

a handle attached to the shaft proximal end of the catheter shaft, wherein the handle has a cavity;

a wire assembly arrangement mounted at the distal section of the catheter shaft, wherein the wire assembly arrangement comprises a plurality of preshaped expandable metallic basket members, wherein at least a portion of the preshaped expandable metallic basket members is essentially straight or coiled adapted for contacting the pre-implanted stent, each metallic basket member having a member distal end, a member proximal end, wherein the member proximal ends of the preshaped expandable metallic basket members are joined at the distal end of the catheter shaft and wherein the member distal ends of the preshaped expandable metallic basket members are joined at a basket distal joint;

a wire assembly deployment mechanism mounted on the handle, wherein the wire assembly deployment mechanism comprises an elongated element inside the at least one lumen of the catheter shaft, wherein a distal end of We elongated element is secured to the basket distal joint, wherein the plurality of preshaped expandable metallic basket members is expanded at a deployed state, and wherein the plurality of preshaped expandable metallic basket members is retracted at a non-deployed state;

a wire guide shaft at the distal section of the catheter shaft, the wire guide shaft having a proximal end and a distal end that the wire guide shaft defines a wire guide lumen, wherein the wire guide lumen has at least one opening at the distal end and at least one opening at the proximal end of the wire guide shaft, wherein the wire guide shaft is used for introducing said medical device system into a vascular vessel over a guidewire; and a RF current generator, wherein the RF current is supplied to the wire assembly arrangement through an electric conductor for contacting a pre-implanted stent, wherein the wire assembly arrangement and the pre-implanted stent forms an electrode arrangement for delivering RF current to a tissue for therapeutic purposes.

10. The medical device system as in claim 9, wherein the plurality of preshaped expandable metallic basket members is expanded by pulling the elongated element toward the handle, and wherein the plurality of preshaped expandable metallic basket members is retracted by pushing the elongated element away from the handle.

11. The medical device system as in claim 9, wherein the wire guide lumen is at one side of the wire guide shaft for rapid exchange of said medical device system over the guidewire.

12. The medical device system as in claim 9, wherein the wire guide lumen is connected to and in communication with the at least one lumen of the catheter shaft, and wherein the wire guide shaft is used for introducing said medical device system over the guidewire.

13. The medical device system as in claim 9 further comprising at least one temperature sensor, wherein the temperature sensor is disposed at close proximity of the wire assembly arrangement of the catheter shaft.

14. The medical device system as in claim 13 further comprising a temperature controller, wherein temperature measured from the temperature sensor is relayed to the temperature controller and is adapted to effect the RF current supply to the medical device system.

15. The medical device system of claim 9, wherein the RF current is within the range of 50 to 2,000 kHz.

16. The medical device system of claim 9, wherein material for the preshaped expandable metallic basket members of the wire assembly arrangement is selected from the group consisting of platinum, iridium, gold, silver, stainless steel, Nitinol, and an alloy of their mixtures.

* * * * *